Figure 1:
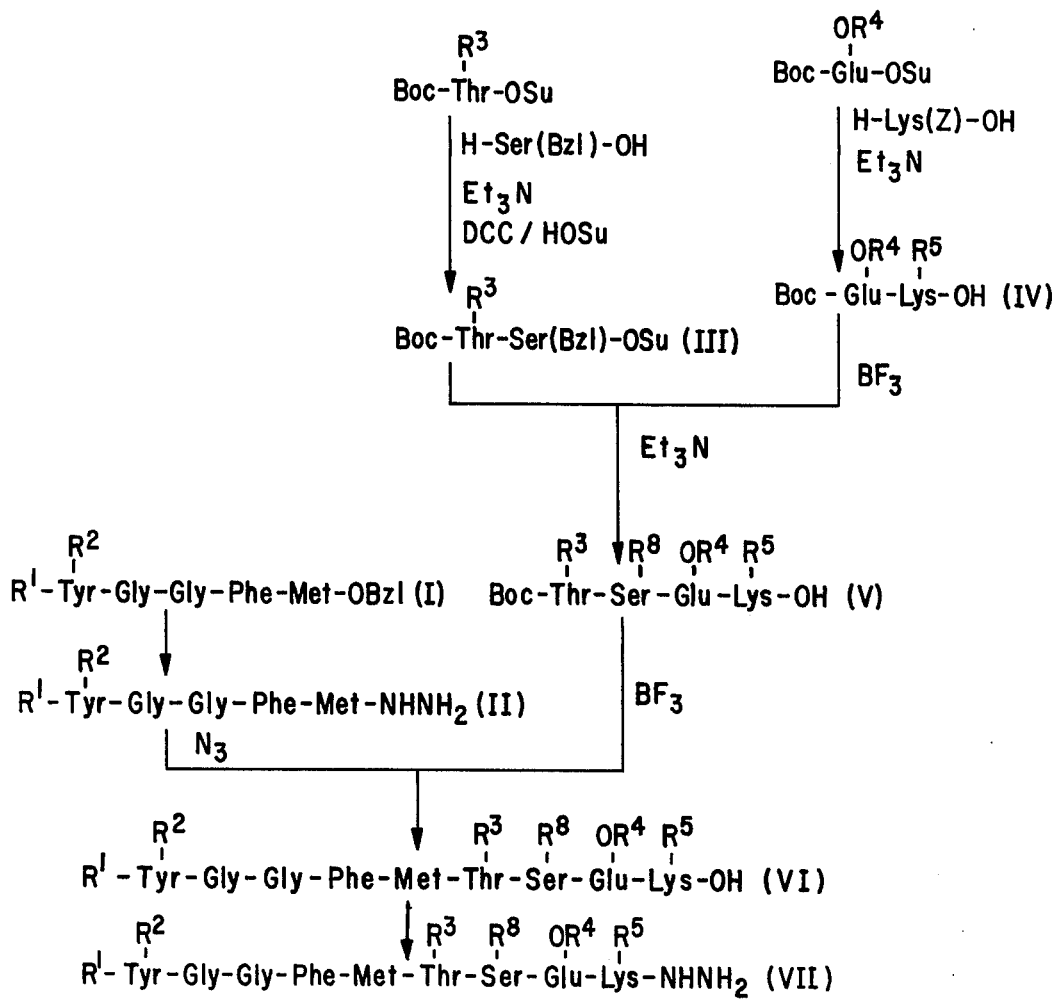
Figure 2:
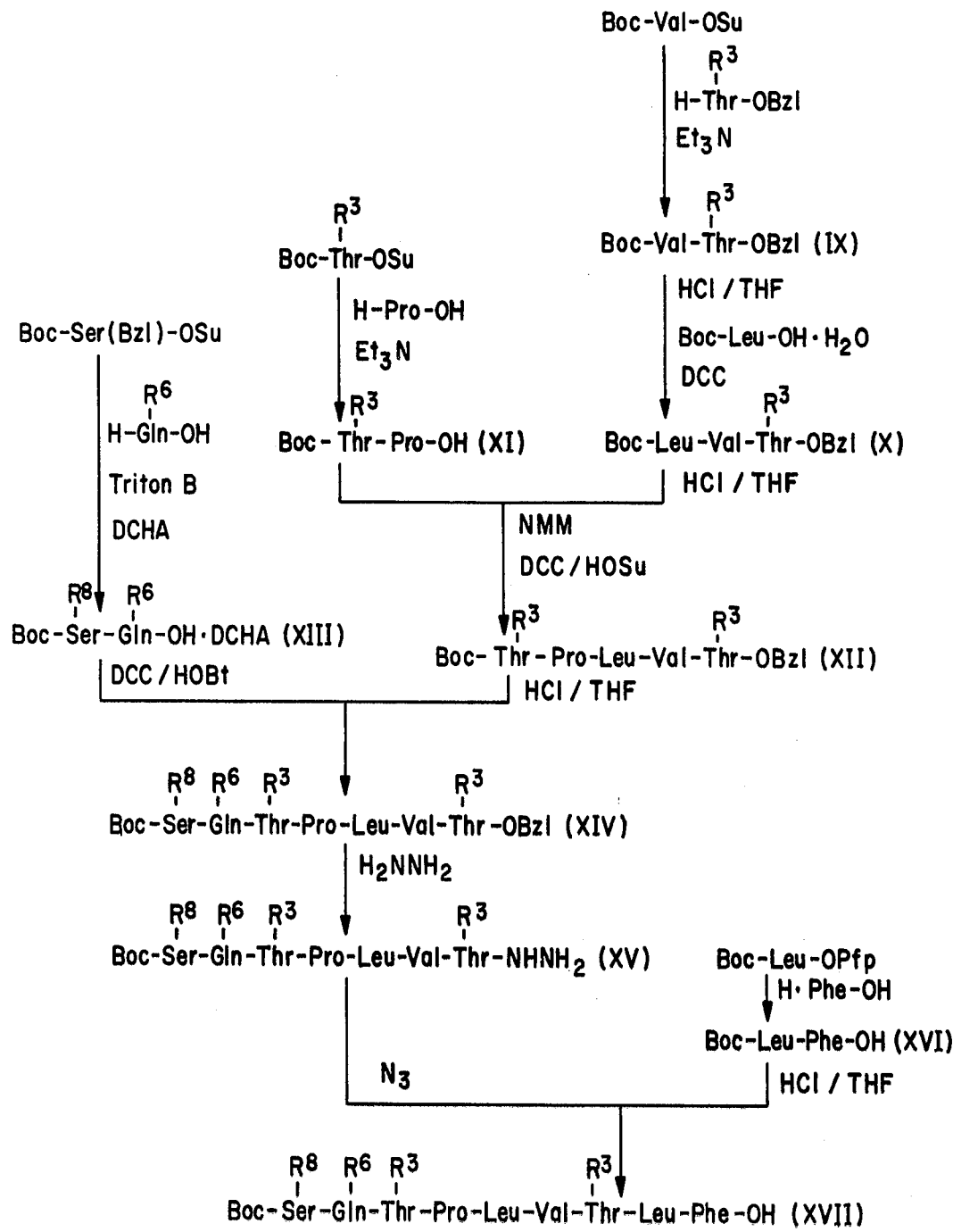
Figure 3:
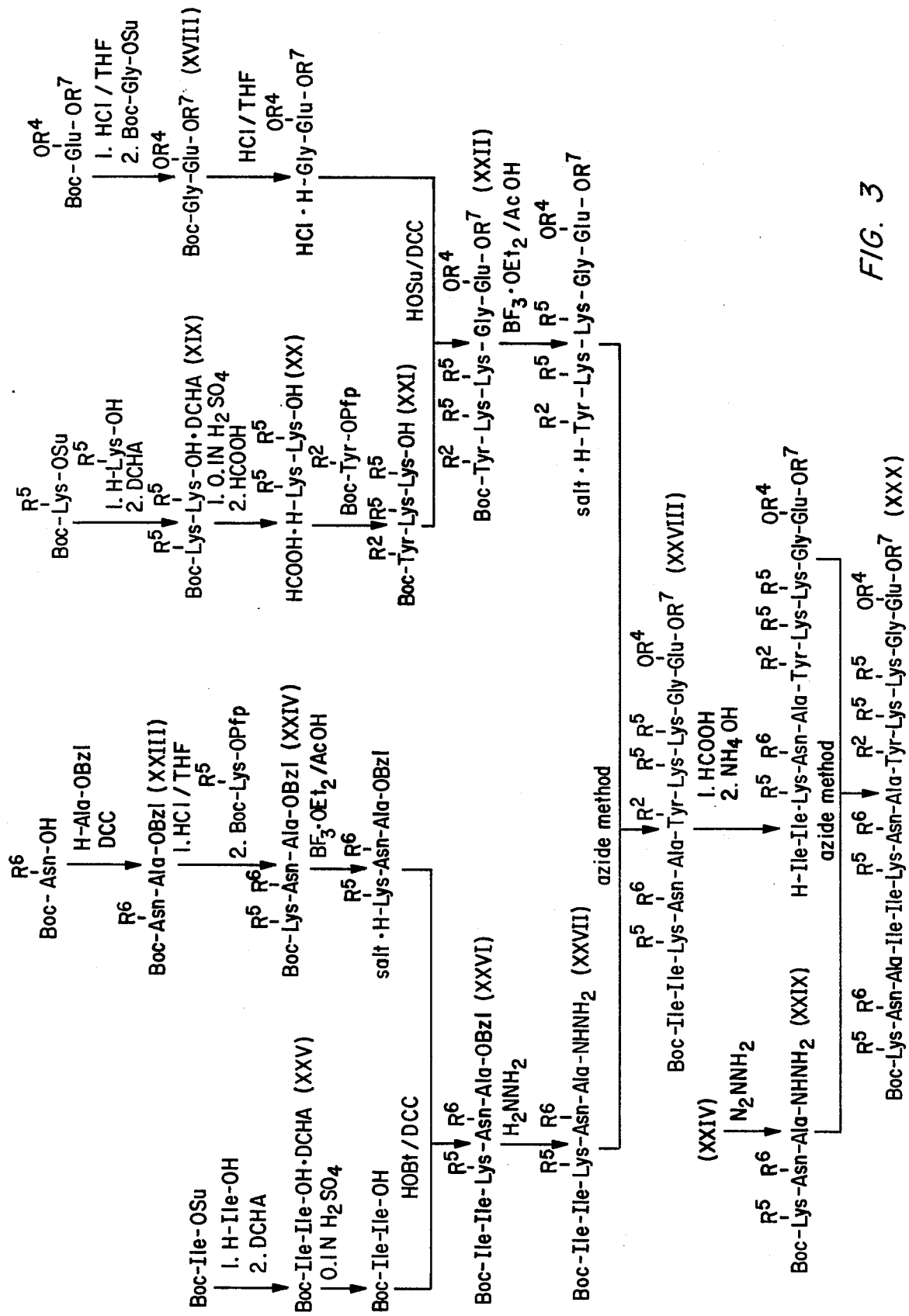
Figure 4:
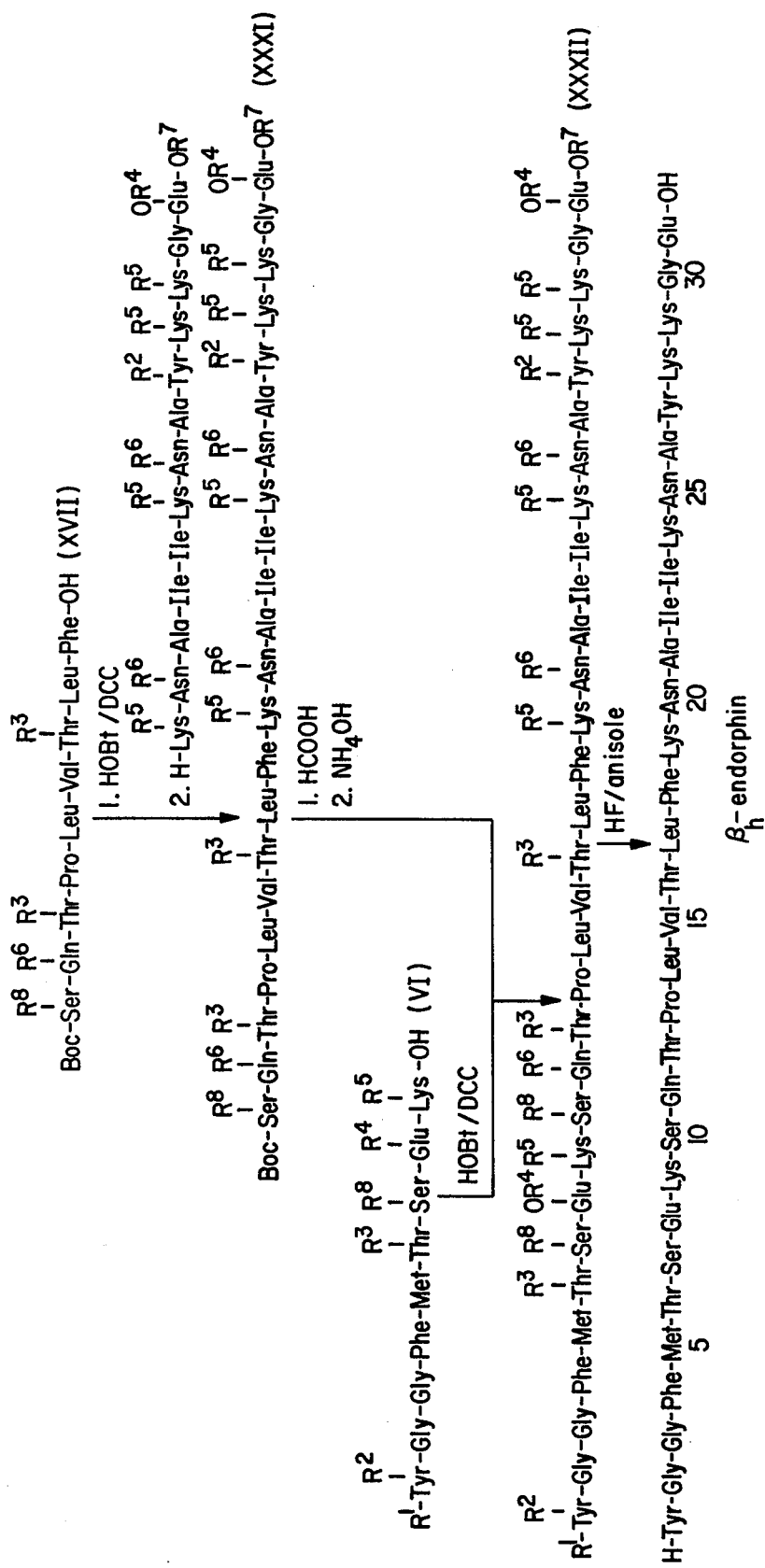

United States Patent [19]

Meienhofer et al.

[11] 4,105,652

[45] Aug. 8, 1978

[54] SYNTHESIS OF HUMAN β-ENDORPHIN

[75] Inventors: Johannes Arnold Meienhofer, Upper Montclair; Su-Sun Wang, Bloomfield, both of N.J.

[73] Assignee: Hoffmann-La Roche Inc., Nutley, N.J.

[21] Appl. No.: 822,120

[22] Filed: Aug. 5, 1977

[51] Int. Cl.² .............................................. C07C 103/52
[52] U.S. Cl. .................................. 260/112.5 R; 260/8
[58] Field of Search ................................. 260/112.5 R

[56] References Cited

U.S. PATENT DOCUMENTS 4,038,222  7/1977  Li .............................. 260/112.5 R

OTHER PUBLICATIONS

Li, et al., J. Med. Chem. 1977, vol. 20, pp. 325-328.

Primary Examiner—Delbert R. Phillips
Attorney, Agent, or Firm—Samuel L. Welt; Jon S. Saxe; George M. Gould

[57] ABSTRACT

Human β-endorphin ($β_h$-endorphin) is prepared by solution phase peptide synthesis. Synthesis proceeded via the protected β-endorphin fragments 1-9, 10-18, 19-21 and 22-31.

14 Claims, 4 Drawing Figures

SYNTHESIS OF HUMAN β-ENDORPHIN

BACKGROUND OF THE INVENTION

Human β-endorphin has been isolated in a highly purified state from human pituitary glands. It is identical with the COOH-terminal 31-residue part of the human β-lipotropin. The structure of human β-endorphin has been confirmed by solid phase synthesis. See in this regard Li et al., J. Med. Chem. 20, 325–328 (1977) and U.S. Pat. No. 4,038,222. β-endorphin has been found to be a potent analgesic when administered directly into the brain and assayed in the tail-flick, hotplate and writhing in mice and in the wet shake test in rats. On a molar basis, β-endorphin is 18–33 times more potent than morphine and its actions are blocked by naloxone. By intravenous administration β-endorphin produces 3–4 times more potent effects than morphine. When administered i.c.v., it mimicks morphine in almost all of its effects, including causation of prolonged cataleptic states, development of tolerance and dependence, respiratory side effects and stimulation of release of somatotropin and prolactin in rats.

Previous synthesis of β-endorphins have been carried out by solid phase methods. A solution synthesis offers the advantage of more efficient scale-up to allow production of amounts needed for clinical evaluations and ultimately commercial production of this compound.

DESCRIPTION OF THE INVENTION

The present invention relates to an improved synthesis of human β-endorphin using solution phase peptide synthesis procedures. A further aspect of the present invention are the novel, protected $\beta_h$-endorphin fragments which are utilized as intermediates in the synthesis as well as the protected thirty one amino acid precursor of $\beta_h$-endorphin.

In a preferred embodiment of the present synthesis, the tert-butyloxycarbonyl (Boc) group was used for the temporary $N^\alpha$-amino protection, the side chain functions were protected by benzyl-derived groups, and the chain assembly proceeded via the intermediated protected fragments 1–9, 10–18, 19–21 and 22–31.

For the synthesis of the amino-terminal protected nonapeptide(1–9), see FIG. I, (VI) or its hydrazide (VII); the pentapeptide derivative II was coupled to the $N^\alpha$-deprotected tetrapeptide V by the azide method. Conversion of VI to VII was carried out with dicyclohexylcarbodiimide in the presence of 1-hydroxybenzotriazole and hydrazine.

FIG. II shows the preparation of intermediate fragment 10–18, (XVII) by an azide condensation of the protected heptapeptide derivative XV with amino deprotected XVI. Compound XV in turn, was obtained via XIV from a dicyclohexylcarbodiimide/1-hydroxybenzotriazole-mediated coupling of the dipeptide derivative XIII with the pentapeptide derivative XII.

Several intermediate fragments were prepared in the synthesis of fragment 19–31, see FIG. III. Dicyclohexylcarbodiimide/N-hydroxysuccinimide-mediated coupling of $N^\alpha$-deprotected dipeptide benzyl ester XVIII with tripeptide derivative XXI provided the protected pentapeptide XXII which, after $N^\alpha$-deprotection, was coupled with the pentapeptide derivative XXVII via the azide method to provide the protected decapeptide derivative XXVIII. Following its $N^\alpha$-deprotection the decapeptide derivative was condensed with the tripeptide intermediate XXIX by the azide method to yield the intermediate protected tridecapeptide XXX which covers sequence region 19–31.

FIG. IV depicts the assembly of the three main intermediate fragments into the desired protected untriakontapeptide XXXII. $N^\alpha$-Protecting group removal from XXX preferably with 98% formic acid was followed by condensation with intermediate nonapeptide derivative XVII by the dicyclohexylcarbodiimide/1-hydroxybenzotriazole procedure to provide the 22-residue protected intermediate XXXI. This material was treated with formic acid in the preferred embodiment to remove the $N^\alpha$-protecting group and coupled with the nonapeptide derivative VI using dicyclohexylcarbodiimide/1-hydroxybenzotriazole as condensing agent and molten phenol and dimethylformamide as solvents. The ensuing protected untriakontapeptide preparation (XXXII) was, without further characterization, treated with liquid hydrogen fluoride in the presence of anisole to remove all protecting groups. Purification of the crude $\beta_h$-endorphin preparation through two successive chromatographic procedures, i.e. Sephadex G-15 gel filtration, followed by either partition chromatography or dextran-supported HPLC provided human $\beta_h$-endorphin.

While specific protecting groups have been employed in describing the synthesis of human $\beta_h$-endorphin, it is within the skill of the art to utilize equivalent protecting groups in such synthesis. Thus, in its broadest aspects the present invention relates to the synthesis of a protected untriakontapeptide of the β-human endorphin sequence of the formula

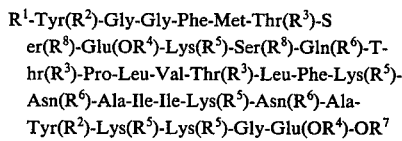

where $R^1$ is a conventional α-amino protecting group selected from benzyloxycarbonyl which may be optionally substituted in the aromatic ring such as by 4-chloro, 2-bromo, 4-bromo, 2,4-dichloro, 4-nitro, 4-methoxy, 3,5-dimethoxy, 4-methyl, 2,4,6-trimethyl, 4-phenylazo, 4-(4'-methoxyphenylazo), 2-(N,N-dimethylcarbonamido), 4-dihydroxyboryl, and 2-nitro-4,5-dimethoxy; urethane type protecting groups such as 4-toluenesulfonylethyloxycarbonyl, 9-fluorenylmethyloxycarbonyl and related base cleavable groups, 5-benzisoxazolylmethylene-oxycarbonyl, methyl thio- and methylsulfonylethyloxycarbonyl, isonicotinyloxycarbonyl, haloethyloxycarbonyl, diisopropylmethyloxycarbonyl, benzhydryloxycarbonyl, isobornyloxycarbonyl, dinitrodiphenylmethyloxycarbonyl, tert.-butyloxycarbonyl, tert.-amyloxycarbonyl, adamantyloxycarbonyl, cyclopentyloxycarbonyl, methylcyclobutyloxycarbonyl, methylcyclohexyloxycarbonyl, 2-arylisopropyloxycarbonyl groups such as 2-(p-biphenylyl)isopropyloxycarbonyl, 2-(4-pyridyl)isopropyloxycarbonyl and related nitrogen containing urethane groups; acyl groups, such as formyl, trifluoroacetyl, phthaloyl, benzenesulfonyl, acetoacetyl, chloroacetyl, 2-nitrobenzoyl, 4-toluenesulfonyl; sulfenyl groups such as benzenesulfenyl, o-nitrophenylsulfenyl and related sulfenyl groups; and aryl-lower alkyl groups such as diphenylmethyl and triphenylmethyl;

$R^2$ is hydrogen or a conventional protecting group for the phenolic hydroxyl group of the tyrosine residue selected from benzyl, 2,6-dichlorobenzyl, benzyloxycarbonyl which may be optionally substituted in the aromatic ring with halo, tert.-butyl and tetrahydropyran-2-yl;

$R^3$ is hydrogen or a conventional protecting group for the hydroxyl group of the threonine residues such as benzyl, acetyl, benzoyl, tert.-butyl, trityl, 2,6-dichlorobenzyl and benzyloxycarbonyl;

$R^4$ is hydrogen or a conventional carboxyl protecting group such as esters selected from aryl esters, such as phenyl or phenyl substituted with lower alkyl, halo, nitro, thio or substituted thio; i.e., methylthio aralkyl esters such as benzyl or benzyl substituted with methoxy, halo or nitro; lower alkyl such as methyl, ethyl, tert.-butyl and tert.-amyl substituted lower alkyl such as 2-haloethyl, $\beta,\beta$-dimethylaminoethyl and cyanomethyl; benzhydryl; and phenacyl;

$R^5$ is a conventional $\omega$-amino protecting group which is independently selected from the protecting groups set forth for $R^1$ above;

$R^6$ is hydrogen or a conventional protecting group for the carboxamide group selected from xanthenyl, 4,4'-dimethoxyhydryl, 4,4'-dimethylbenzhydryl, benzylhydryl and tert.butyl;

$R^7$ is hydrogen or a conventional carboxyl protecting group which is independently selected from the protecting groups set forth for $R^4$ above; and $R^8$ is hydrogen or a conventional protecting group for the hydroxyl group of the serine residues which independently selected from the protecting groups set forth for $R^3$ above and subsequent removal of the protecting groups.

It is also within the scope of the present invention to substitute methionine sulfoxide for the Met residue herein. Methionine sulfoxide can be reduced to Met in a manner known per se, such as by using a chemical reducing agent, preferably mercaptans such as mercaptoethanol.

The removal of protecting groups described above can be carried out by procedures well known in the art such as reduction with sodium in liquid ammonia, hydrogenolysis (for instance, in the presence of a palladium black catalyst), treatment with hydrohalic acid (such as hydrobromic, hydrofluoric or hydrochloric acids) in acetic acid, treatment with trifluoroacetic acid or treatment with appropriate inorganic or organic bases such as sodium hydroxide, potassium hydroxide or piperidine.

In a preferred embodiment $R^1$ is benzyloxycarbonyl, $R^2$ is hydrogen, $R^3$ is benzyl, $R^4$ is benzyl, $R^5$ is benzyloxycarbonyl, $R^6$ is hydrogen, $R^7$ is benzyl and $R^8$ is benzyl.

It should be noted that in the early steps of the synthesis shown in the Figures, the Boc protecting group is shown for protecting the N-terminal $\alpha$-amino group in a number of the intermediates. Should, however, it be desirable to select the Boc or related groups to protect side chain functional groups, it would, of course, be necessary to utilize an alternate conventional N-terminal $\alpha$-amino protecting group which is selectively cleavable from the Boc or related groups.

The process and intermediates of the present invention are further illustrated by the following Examples. In such examples all optically active amino acids have the L-configuration and the solvent systems were as follows:

1-butanol—acetic acid—water (4:1:1)
1-butanol—pyridine—acetic acid—water (15:10:3:12)
1-butanol—ethyl acetate—acetic acid—water (1:1:1:1)
chloroform—methanol—acetic acid (85:10:5)
chloroform—methanol (50:10) or (90:10)

EXAMPLE 1

Z-Tyr-Gly-Gly-Phe-Met-NHNH$_2$ (II)

Compound I, Z-Tyr-Gly-Gly-Phe-Met-OBzl (0.85 g, 1.07 mmol) was dissolved in DMF (10 ml, purged with Argon for 15 min) and treated with 0.34 ml of H$_2$NNH$_2$ for 72 hr. at 25° C. The solvent was removed under reduced pressure to yield a crystalline residue which was triturated with H$_2$O to form a crystalline product, yield 0.65g (84.2%). Recrystallized from DMF and ethanol to give colorless needles; mp 209°–213° C.; $[\alpha]_D^{25}$ −27.6° (c 1, DMF). Anal. Calcd for C$_{35}$H$_{43}$N$_7$O$_8$S$_1$ (721.84): C, 58.24; H, 6.00; N, 13.58; S, 4.44. Found: C, 57.50; H, 6.04; N, 13.75; S, 4.67.

EXAMPLE 2

Boc-Thr(Bzl)-Ser(Bzl)-OSu (III)

A suspension of H-Ser(Bzl)-OH (2.59 g, 13.28 mmol) in DMF (70 ml) was stirred with Et$_3$N (2.0 ml) and Boc-Thr(Bzl)-OSu (6.0 g, 14.76 mmol) at 0° C for 2 hr and 25° C for 72 hr. The reaction mixture was acidified to about pH 3 with acetic acid and the solvents removed under reduced pressure. The resulting clear oil was extracted into ethyl acetate, washed with 5% AcOH and water, dried (MgSO$_4$) and evaporated to a clear oil. The oil was dissolved in THF (100 ml) and treated with HOSu (1.8 g) and dicyclohexylcarbodiimide (DCC) (3.0 g) for 1.5 hr at 0° C and 25° C for 3 hr. The DCU was removed by filtration and the filtrate evaporated to a clear oil which was crystallized from ETOH, yield 5.3 g (70.4%); mp 112°–113° C; $[\alpha]_D^{25}$ +18.7° (c 1, CHCl$_3$).

EXAMPLE 3

Boc-Glu(OBzl)-Lys(Z)-OH (IV)

A suspension of H-Lys(Z)-OH (0.89 g, 3.18 mmol) in DMF (25 ml) was stirred with Et$_3$N (0.5 ml) and Boc-Glu(OBzl)-OSu (1.58 g, 3.5 mmol) at 0° C for 1 hr and 25° C for 24 hr. The reaction mixture was worked up as described above in Example 2 to produce a clear oil which was crystallized from EtOAc and petroleum ether to yield 1.47 g (77.4%); mp 110°–112° C.; $[\alpha]_D^{25}$ +6.0° (c 1, CHCl$_3$). Anal. Calcd for C$_{31}$H$_{41}$N$_3$O$_9$ (599.69): C, 62.08; H, 6.89; N, 7.00. Found: C, 62.04; H, 6.96; N, 7.10.

EXAMPLE 4

Boc-Thr(Bzl)-Ser(Bzl)-Glu(OBzl)-Lys(Z)-OH (V)

Compound IV (2.0 g, 3.33 mmol) was dissolved in 0.4 M BF$_3$.OEt$_2$ in acetic acid (16.7 ml) and stirred at 25° C. for 4 hr. The solution was evaporated to a clear oil which was solidified by treatment with dry ether and drying over KOH. This material was dissolved in DMF (25 ml) and reacted with Et$_3$N (0.47 ml) and Boc-Thr(Bzl)-Ser(Bzl)-OSu (1.89 g, 3.33 mmol) at 0° C for 1.5 hr and 25° C for 24 hr. The pH was adjusted to 8.0 (by wet pH paper) with Et$_3$N when necessary during the course of reaction. The reaction was worked up as described above in Example 2 to yield a crystalline product from EtOAc and petroleum ether, yield 2.5 g (78.1%); mp 111°–115° C; $[\alpha]_D^{25}$ −4.8° (c 1, CHCl$_3$). Anal. Calcd for C$_{52}$H$_{65}$N$_5$O$_{13}$ (968.12): C, 64.51; H, 6.76; N, 7.23. Found: C, 64.40; H, 6.60; N, 7.11.

EXAMPLE 5

Z-Tyr-Gly-Gly-Phe-Met-Thr(Bzl)-Ser(Bzl)-Glu(OBzl)-Lys(Z)-OH (VI)

Compound V (4.2 g, 4.33 mmol) was treated with 0.4 M $BF_3 \cdot OEt_2$ in acetic acid (27 ml) for 3.75 hr. The solvent was evaporated to a clear oil which was solidified by treatment with dry ether and drying over KOH.

Compound II (3.13 g, 4.33 mmol) was dissolved in DMF (50 ml, purged with Argon for 15 min), cooled to −20° C and treated with 5.93 ml of 4 N HCl in THF followed by 0.88 ml of i-amylnitrite. After 30 min, the mixture was cooled down to −30° C and 3.64 ml of $Et_3N$ and H-Thr(Bzl)-Ser(Bzl)-Glu(OBzl)-Lys(Z)-OH were added. The mixture was stirred at 4° C for 72 hours during which time some more $Et_3N$ was added in order to maintain the pH between 7 and 8. The reaction was acidified to pH 3 with acetic acid. Evaporation of the solvent and trituration of the residue in water gave a white glassy product which was washed with 5% AcOH and water; it was then triturated in EtOH several times and dried, yield 5.5 g (81.5%); mp 227°–231° C dec. $[\alpha]_D^{25}$ −3.2° (c 1, DMF). Anal. Calcd for $C_{82}H_{96}N_{10}O_{19}S$ (1157.79): C, 63.22; H, 6.21; N, 8.99; S, 2.06. Found: C, 63.03; H, 6.24; N, 9.12; S, 2.12. Amino acid Analysis (6N HCl/phenol, 100° C, 24 hr): Lys, 1.11; Thr, 1.05; Ser, 0.86; Glu, 1.07; Gly, 1.86; Met, 0.95; Tyr, 0.81; Phe, 1.02.

EXAMPLE 6

Z-Tyr-Gly-Gly-Phe-Met-Thr(Bzl)-Ser(Bzl)-Glu(OBzl)-Lys(Z)-NHNH$_2$ (VII)

Compound VI (0.1 g, 0.064 mmol) was dissolved in DMF (2 ml) and stirred with $H_2NNH_2$ (5 μl in a few drops DMF), HOBt 0.0196 g and DCC 0.0145 g at 0° C for 1 hr and 25° C for 24 hrs. During this time a few drops of N-methylmorpholine (NMM) was added to the reaction to maintain a pH between 7–8. The reaction mixture was added dropwise to rapidly stirring water to form a white precipitate which was filtered and washed with $H_2O$ and $Et_2O$; it was recrystallized from DMF and EtOH, yield 0.067 g (67%); mp 245°–249° dec.; $[\alpha]_D^{25}$ −4.3° (c 1, DMF). Anal. Calcd for $C_{82}H_{98}N_{12}O_{18}S$ (1571.82): C, 62.66; H, 6.28; N, 10.69; S, 2.04. Found: C, 62.78; H, 6.35; N, 10.61; S, 2.03.

EXAMPLE 7

Boc-Val-Thr(Bzl)-OH (VIII)

A suspension of H-Thr(Bzl)-OH (3.0 g, 14.34 mmol) in DMF (60 ml) was mixed with $Et_3N$ (2 ml) and Boc-Val-OSu (4.96 g, 15.78 mmol) at 0° C for 2 hours and then at 25° C for 24 hours. Acetic acid was added to about pH 3 and the solvents removed under reduced pressure. The product was extracted into EtOAc, washed with 5% AcOH and water, dried (MgSO$_4$) and evaporated to clear oil which crystallized from EtOAc with petroleum ether to yield 4.9 g (83.1%); mp 132°–135° C; $[\alpha]_D^{25}$ +21.5° (c, 1, CHCl$_3$). Anal. Calcd for $C_{21}H_{32}N_2O_6$ (408.49): C, 61.74; H, 7.89; N, 6.85. Found: C, 61.61; H, 7.76; N, 6.80.

EXAMPLE 8

Boc-Val-Thr(Bzl)-OBzl (IX)

H-Thr(Bzl)-OBzl hemioxalate (58 g, 168.4 mmol) was suspended in DMF (700 ml) and stirred with Boc-Val-OSu (48 g, 153.1 mmol) and $Et_3N$ (16 ml) at 0° C for 1 hr, 4° C for 72 hrs and 25° C for 24 hrs. It was necessary during this time to add at intervals additional $Et_3N$ in order to maintain the pH between 7 and 8. The reaction mixture was worked up as in Example 2 to yield an oil which crystallized from EtOAc with petroleum ether, yield 40.8 g (53.5%); mp 99°–100.5° C; $[\alpha]_D^{25}$ −26.0° (c 1, MeOH). Anal. Calcd for $C_{28}H_{38}N_2O_6$ (498.62): C, 67.45; H, 7.68; N, 5.62. Found: C, 67.57; H, 7.55; N, 5.70.

EXAMPLE 9

Boc-Leu-Val-Thr(Bzl)-OBzl (X)

Compound VIII (1.0 g, 2.45 mmol) was treated with 4 N HCl in THF for 15 minutes. Evaporation of the excess HCl and solvent and treatment with dry ether afforded an amorphous white solid, 0.65 g (77.4%).

The HCl salt (0.65 g, 1.89 mmol) was dissolved in DMF (15 ml) and stirred with $Et_3N$ (0.27 ml) and Boc-Leu-OSu (0.62g, 1.89 mmol) at 0° C for 1.5 hr and 25° C for 24 hr. During this time some additional $Et_3N$ was added occassionally to maintain the pH between 7 and 8. The reaction mixture was worked up in as in Example 2 to yield an amorphous solid. The free acid without further characterization was converted to its benzyl ester through the cesium salt method as described by Wang et al., J. Org. Chem., 42, 1286 (1977) to give a clear oil, yield 0.9 g (77.9%); $[\alpha]_D^{25}$ −31.0° (c 1, CHCl$_3$). Anal. Calcd for $C_{34}H_{49}N_3O_7$ (611.79): C, 66.75; H, 8.07; N, 6.86. Found: C, 66.71; H, 8.08; N, 6.61.

Compound X was also prepared in the following manner: Compound IX (40.0 g, 80.23 mmol) was treated with 4 N HCl in THF for 20 minutes. Evaporation of the excess HCl and solvent and treatment with dry ether afforded an amorphous white solid, 28.0 g (80.1%).

The HCl salt (28.0 g, 64.3 mmol) was dissolved in DMF (150 ml) and stirred with $Et_3N$ (9 ml), Boc-Leu-OH.H$_2$O (16.0 g, 64.3 mmol) and DCC (14.6 g) at 0° C for 1 hour and 25° C for 24 hours. The reaction mixture was worked up in the usual manner to an oil, yield 33.0 g (83.9%). The oil was subjected to silica gel chromatography with a stepwise gradient elution in the solvent system, chlorobutane and acetonitrile to afford a product with analysis (tlc) as that of the above preparation.

EXAMPLE 10

Boc-Thr(Bzl)-Pro-OH (XI)

A suspension of H-Pro-OH (1.0 g, 8.69 mmol) in DMF (15 ml) was stirred with $Et_3N$ (2.44 ml) and Boc-Thr(Bzl)-OSu (3.88 g, 9.56 mmol) at 0° C for 1 hr and 25° C for 72 hrs. The reaction was acidified to pH 3 with acetic acid and worked up as described in Example 2 to produce a crystalline product from EtOAc and petroleum ether: 3.0 g (85.0%); mp 84°–88° C; $[\alpha]_D^{25}$ −52.2° (c 1, CHCl$_3$). Anal. Calcd for $C_{21}H_{30}N_2O_6$ (406.48): C, 62.05; H, 7.43; N, 6.89. Found: C, 62.29; H, 7.52; N, 6.86.

EXAMPLE 11

Boc-Thr(Bzl)-Pro-Leu-Val-Thr(Bzl)-OBzl (XII)

Boc-Leu-Val-Thr(Bzl)-OBzl (0.88 g, 1.43 mmol) was treated with 4 N HCl in THF for 45 minutes. Evaporation of the excess HCl and solvent and treatment with dry ether gave an amorphous white solid, 0.55 g (70.5%).

The HCl salt (0.55 g, 1.0 mmol) was dissolved in DMF (20 ml) and stirred with NMM (0.11 ml), Boc-Thr(Bzl)-Pro-OH (0.407 g, 1.0 mmol), HOSu (0.23 g)

and DCC (0.227 g) at 0° C for 1.5 hr and 25° C for 24 hr. The by-products were filtered off and the filtrate was evaporated to dryness. The residue was dissolved in EtOAc. The organic phase was washed with 5% AcOH, $H_2O$, 5% $NaHCO_3$, $H_2O$, dried ($Na_2SO_4$) and evaporated to dryness. The product (XII) was obtained as an amorphous solid after silica gel chromatography [System $CHCl_3$:MeOH (9:0.5)] 0.6 g (66.7%); $[\alpha]_D^{25}$ 44.0° (c 1, $CHCl_3$). Anal. Calcd for $C_{50}H_{69}N_5O_{10}$ (900.14): C, 66.72; H, 7.73; N, 7.78. Found: C, 66.73; H, 7.52; N, 7.71.

EXAMPLE 12

Boc-Ser(Bzl)-Gln-OH.DCHA (XIII)

Glutamine (15.0 g, 104.2 mmol) was dissolved in 51.5 ml of 40% Triton B and evaporated to an oil. It was re-evaporated twice with DMF and the salt obtained was stirred with Boc-Ser(Bzl)-OSu (45.0 g, 114.6 mmol) in DMF (400 ml) at 0° C for 2 hours and 25° C for 24 hours. The solvent was evaporated to give a syrup which was dissolved in chloroform, washed with 5% HOAc and water, dried ($Na_2SO_4$) and evaporated to yield an oil. The oil was dissolved in ethyl acetate (500 ml) and titrated with dicyclohexylamine to pH 8–9. The resulting crystals were filtered away, washed with EtOAc and $Et_2O$ and dried, yield 39.4 g (62.5%); mp 124°–127° C; $[\alpha]_D^{25}$ +8.30 (c 1, MeOH). Anal. Calcd for $C_{32}H_{52}N_4O_7$ (604.79): C, 63.55; H, 8.67; N, 9.26. Found: C, 63.28; H, 8.82; N, 9.07.

EXAMPLE 13

Boc-Ser(Bzl)-Gln-Thr(Bzl)-Pro-Leu-Val-Thr(Bzl)-OBzl (XIV)

Compound XII (1.0 g, 1.11 mmol) was treated with 4 N HCl in THF for 45 min. Evaporation of the excess HCl and solvent and treatment with dry ether gave an amorphous white solid, 0.84 g (92.9%). The protected pentapeptide HCl salt (0.76 g, 0.91 mmol) was dissolved in DMF (20 ml) and stirred with NMM (0.10 ml), Boc-Ser(Bzl)-Gln-OH (0.385 g, 0.91 mmol) obtained by partitioning the corresponding DCHA salt (0.6 g, 0.99 mmol) between aqueous $H_2SO_4$ and EtOAc, HOBt (0.246 g) and DCC (0.206 g) at 0° C for 2 hrs and 25° C for 24 hrs. The reaction was worked up as described in Example 11. A crystalline product was obtained from isopropyl alcohol: 0.608 g (55.4%); mp 157°–159° C; $[\alpha]_D^{25}$ −44.7° (c 1, $CHCl_3$). Anal. Calcd for $C_{65}H_{88}N_8O_{14}$ (1205.47): C, 64.77; H, 7.36; N, 9.29. Found: C, 64.84; H, 7.50; N, 9.13. Amino Acid Analysis: (6 N HCl/phenol, 110° C, 24 hrs.) Thr 1.90, Ser 0.78, Glu 0.99, Pro 0.99, Val 1.04, Leu 1.04.

EXAMPLE 14

Boc-Ser(Bzl)-Gln-Thr(Bzl)-Pro-Leu-Val-Thr(Bzl)-NHNH$_2$ (XV)

Compound XIV (1.6 g, 1.32 mmol) was dissolved in DMF/MeOH (5:3; 16 ml) and treated with $H_2NNH_2$ (0.78 ml) for 72 hrs at 25° C. The white solid was filtered and washed with MeOH and water, yield 1.05 g (70.5%); mp 210°–210.5° C; $[\alpha]_D^{25}$ −22.5° (c 1, DMF). Anal. Calcd for $C_{58}H_{84}N_{10}O_{13}$ (1129.37): C, 61.68; H, 7.50; N, 12.40. Found: C, 61.72; H, 7.26; N, 12.30.

EXAMPLE 15

Boc-Leu-Phe-OH (XVI)

H-Phe-OH (1.49 g, 9 mmol) fine powder was suspended in DMF (20 ml). After cooling at 0°, $Et_3N$ (1.26 ml, 9 mmol) was added, followed by Boc-Leu-pentafluorophenylester, i.e., Boc-Leu-OPfp (3.93 g, 9.9 mmol). It was stirred for 1 hr at 0° C and for 2.5 hr at room temperature. After filtration the solvent was evaporated and the residue was treated with $H_2O$. The separated oil was extracted with EtOAc. The organic phase was washed with 10% citric acid, $H_2O$, dried ($Na_2SO_4$) and evaporated to a smaller volume. Addition of petroleum ether and standing overnight in the refrigerator provided the product (XVI) which was recrystallized from EtOAc-petroleum ether to fine crystals, yield 2.3 g (67.6%); mp 104°–106° C; $[\alpha]_D^{25}$ −3.40° (c 1, EtOH). Anal. Calcd for $C_{20}H_{30}N_2O_5$ (378.476): C, 63.47; H, 7.99; N, 7.40. Found: C, 63.46; H, 8.18; N, 7.49.

EXAMPLE 16

Boc-Ser(Bzl)-Gln-Thr(Bzl)-Pro-Leu-Val-Thr(Bzl)-Leu-Phe-OH (XVII)

Boc-Leu-Phe-OH (XVI) (0.53 g, 1.4 mmol) was deblocked with 4 N HCl/THF (17.5 ml) and worked up as in Example 9 to yield the white crystalline salt. Boc-Ser(Bzl)-Gln-Thr(Bzl)-Pro-Leu-Val-Thr(Bzl)-NHNH$_2$ (XV) (0.79 g, 0.7 mmol) in DMF (10 ml) was converted into the azide by treatment with 2.8 N HCl/THF (1.25 ml) and i-amylnitrite (0.14 ml) at −20° C for 25 min. The temperature was lowered to −30° C, $Et_3N$ (0.49 ml) was added followed by a pre-cooled mixture of the hydrochloride salt of compound (XVI) which was pretreated with $Et_3N$. The mixture was stirred for 1.5 hr at −15° C and for 4 days at 4° C. It was acidified with glacial AcOH, evaporated to a smaller volume, and treated with 1 M AcOH. The precipitated solid was filtered and washed with $H_2O$. The crude product (0.92 g) mp 194°–196.5° C, after trituration with EtOAc, was recrystallized from hot MeOH to provide (XVII) in fine crystals, 0.51 g (53%); mp 205°–207° C; $[\alpha]_D^{25}$ −20.1° (C 1, DMF). Anal. Calcd for $C_{73}H_{102}N_{10}O_{16}$ (1375.70): C, 63.73; H, 7.47; N, 10.18. Found: C, 63.26; H, 7.43; N, 10.23. Amino Acid Analysis (6 N HCl-phenol, 100° C, 24 hr): Thr$_{2.00}$, Ser$_{0.91}$, Glu$_{1.03}$, Pro$_{1.05}$, Val$_{0.99}$, Leu$_{2.08}$, Phe$_{1.00}$.

EXAMPLE 17

Boc-Gly-Glu(OBzl)-OBzl (XVIII)

To a stirred solution at 0° C, of HCl.H-Glu(OBzl)-OBzl (1.82 g, 5 mmol) in DMF (35 ml), $Et_3N$ (0.7 ml) was added dropwise followed by Boc-Gly-OSu (1.5 g, 5.5 mmol). The mixture was stirrred at 0° C for 2 hr and at room temperature overnight; pH 8 was maintained by addition of a few drops of $Et_3N$. The reaction mixture was then evaporated to a small volume and $H_2O$ was added. The precipitated oil was extracted with EtOAc and the organic phase was washed with 1 M AcOH, water, and dried ($Na_2SO_4$). Evaporation provided an oil which was purified on a Silica gel 60 column using $CHCl_3$:MeOH (5:1) as eluant. The pooled fractions containing (XVIII) were evaporated yielding colorless oil which failed to crystallize, 1.62 g (67%) homogeneous on tlc $[\alpha]_D^{25}$ −15.0° (c 2, MeOH). Anal. Calcd for $C_{26}H_{32}N_2O_7$ (484.558): C, 64.45; H, 6.66; N, 5.78. Found: C, 64.23; H, 6.72; N, 5.66. Compound XVIII was also prepared from Boc-Gly-Glu(OBzl)-OH via the cesium salt procedure of Wang et al, supra.

EXAMPLE 18

Boc-Lys(Z)-Lys(Z)-OH.DCHA (XIX)

H-Lys(Z)-OH (17.57 g, 62.7 mmol) was added to a cold (0°) stirred solution of Boc-Lys(Z)-OSu (36.25 g, 65.8 mmol) in DMF (500 ml.) After dropwise addition of Et$_3$N (8.8 ml, 62.7 mmol), the mixture was stirred for 1 hr at 0° and for 2 days at room temperature during which time the pH was kept between 7 and 8 by addition of Et$_3$N. After filtration, the solvent was evaporated and the residual oil was treated with 5% aqueous AcOH. After decantation of the aqueous phase the remaining oil was washed twice with water and dissolved in EtOAc. The organic layer was dried (Na$_2$SO$_4$) and evaporated to a volume of 600 ml. It was titrated with DCHA to pH 8. After standing overnight at 4° C, the precipitated crystalline salt was collected by filtration and washed with cold EtOAc and then with petroleum ether, yield 48.5 g; mp 162°–163° C. Recrystallization from MeOH/ether provided 40 g (81%); mp 165°–166° C; $[\alpha]_D^{25}$ −2.2° (c 1, MeOH). Anal. Calcd for C$_{45}$H$_{69}$N$_5$O$_9$(824.087): C, 65.59; H, 8.44; N, 8.50. Found: C, 65.40; H, 8.50; N, 8.39. An identical product was obtained when Boc-Lys(Z)-OPfp was reacted with H-Lys(Z)-OH for 4.5 hr.

EXAMPLE 19

H-Lys(Z)-Lys(Z)-OH.HCOOH (XX)

Boc-Lys(Z)-Lys(Z)-OH.DCHA (0.82 g, 1 mmol) was partitioned between EtOAc and 0.1 N H$_2$SO$_4$. The aqueous layer was extracted once more with EtOAc and the combined extracts were washed (3 × H$_2$O), dried (Na$_2$SO$_4$) and evaporated to dryness. The oily residue was treated with 93% HCOOH (2.63 ml) at room temperature for 5 hr and evaporated to dryness. It was re-evaporated from H$_2$O and then from DMF. Addition of ether produced a white crystalline solid which after filtering, was treated with EtOH, yield 0.42 g (71%); mp 210°–213° C; $[\alpha]_D^{25}$ +3.88° (c 1.5, DMF). Anal. Calcd for C$_{29}$H$_{40}$N$_4$O$_9$ (588.67): C, 59.17; H, 6.85; N, 9.52. Found: C, 59.41; H, 6.70; N, 9.76.

EXAMPLE 20

Boc-Tyr(Bzl)-Lys(Z)-Lys(Z)-OH (XXI)

A solution of H-Lys(Z)-Lys(Z)-OH.HCOOH (0.23 g, 4 mmol) in DMF (25 ml) was cooled to 0°. Et$_3$N was added dropwise to pH 8.5. Boc-Tyr(Bzl)-OPfp (0.24 g, 0.44 mmol) was then added. After stirring for 1 hr at 0° and 1 hr at room temperature, the reaction mixture was evaporated and the residue was treated with 10% aqueous citric acid. The product was extracted with EtOAc and the organic phase was washed with 10% citric acid, H$_2$O, dried (Na$_2$SO$_4$), and evaporated to a smaller volume. The precipitated white solid was filtered off to yield 0.132 g; mp 171°–174° C. The filtrate was treated with petroleum ether until cloudiness developed. A second fraction was obtained by cooling and thorough trituration of the ensuing precipitate with refluxing EtOAc; 0.16 g; mp 170°–174° C. The combined fractions were again triturated with hot EtOAc to yield 0.27 g (75%); mp 174°–175.5° C; $[\alpha]_D^{25}$ +1.4° (c 1, MeOH). Anal. Calcd for C$_{49}$H$_{61}$O$_{11}$H$_5$ H$_2$O: C, 64.46; H, 6.95; N, 7.67. Found: C, 64.60; H, 6.76; H, 7.61. An identical product was obtained by coupling of Boc-Tyr(Bzl)-OPfp with the salt formed by treatment of Boc-Lys(Z)-Lys(Z)-OH with BF$_3$.OEt$_2$, 0.4 M in AcOH.

EXAMPLE 21

Boc-Tyr(Bzl)-Lys(Z)-Lys(Z)-Gly-Glu(OBzl)-OBzl (XXII)

Boc-Gly-Glu(OBzl)-OBzl (XVIII) (0.28 g, 0.57 mmol) was treated with freshly prepared 4 N HCl in THF (6 ml) for 30 minutes at room temperature. The excess acid and solvent were evaporated and the remaining syrup re-evaporated twice from fresh THF. The residue was solidified by treatment with petroleum ether. The hydrochloride salt was dissolved in DMF (1.5 ml), the solution was cooled to 0° C, and neutralized with NMM (0.06 ml, 0.53 mmol). To this mixture, HOSu (0.12 g, 1.06 mmol) was added followed by a solution of Boc-Tyr(Bzl)-Lys(Z)-Lys(Z)-OH (XXI) (0.48 g, 0.53 mmol) in DMF (3 ml) and by DCC (0.12 g, 0.58 mmol). The reaction was adjusted to pH 7.5 (wet pH paper) with a few drops of NMM and was stirred for 1 hr at 0° C and overnight at room temperature. The insoluble by-products were filtered off and the filtrate was evaporatd to a small volume. The residue was treated with H$_2$O and the precipitated white solid was taken up in CHCl$_3$. The organic phase was washed with (10%) citric acid; H$_2$O, 5% NaHCO$_3$, H$_2$O, dried (Na$_2$SO$_4$), and evaporated to dryness. It was redissolved in CHCl$_3$ and precipitated as a solid powder with petroleum ether. The crude product (0.56 g) was purified on a Silica gel 60 column using 5% MeOH in CHCl$_3$ as eluant. The pooled fractions containing (XXII) were concentrated to a small volume. Precipitation with petroleum ether provided 7.9 g (57.4%) of crystalline material; mp 154°–157° C. Recrystallized from isopropanol or DMF-H$_2$O; mp 157°–159° C; $[\alpha]_D^{25}$ −7.2° (c 1.65, DMF). Anal. Calcd for C$_{70}$H$_{83}$N$_7$O$_{15}$ (1262.49): C, 66.60; H, 6.63; N, 7.77. Found: C, 66.76; H, 6.66; N, 7.84.

EXAMPLE 22

Boc-Asn-Ala-OBzl (XXIII)

The HCl salt of H-Ala-OBzl (43 g, 200 mmol) was dissolved in DMF (500 ml) and stirred with Boc-Asn-OH (46.5 g, 200 mmol), NMM (27 ml), HOBt (54 g), and DCC (45 g) at 0° C for 1.5 hr and 25° C for 17 hr. The reaction mixture was worked up as in Example 11 to a solid which was crystallized from tetrahydrofuran and minimum petroleum ether: 62.5 g (79.4%); mp 140°–141° C; $[\alpha]_D^{25}$ −31.1° (c 1, MeOH). Anal. Calcd for C$_{19}$H$_{27}$N$_3$O$_6$ (393.44): C, 58.00; H, 6.92; N, 10.68. Found: C, 57.77; H, 7.09; N, 10.52.

EXAMPLE 23

Boc-Lys-Asn-Ala-OBzl (XXIV)

Boc-Asn-Ala-OBzl (XXIII) (27.54 g, 70 mmol) was treated with 4 N HCl/THF (875 ml) for 30 minutes at room temperature. Evaporation and treatment with dry ether provided 23.08 g (100%). The hydrochloride salt was dissolved in DMF (250 ml), cooled to 0° C and NMM (4.9 ml, 70 mmol) was added under stirring followed by Boc-Lys(Z)-OPfp (39.5 g, 72.3 mmol). The mixture was stirred for 1 hr at 0° C and 3 hr at room temperature. After evaporation of the solvent to a smaller volume, 0.5 N HCl was added and the precipitated product was collected by filtration and washed on the funnel with H$_2$O, (5%) NaHCO$_3$ and H$_2$O. After drying, it was triturated with EtOAc and then with petroleum ether, yield 41.5 g (90.4%); mp 148°–150° C; $[\alpha]_D^{25}$ −15.3° (c 2, DMF). Anal. Calcd for C$_{33}$H$_{45}$N$_5$O$_9$ (655.76): C, 60.44; H, 6.92; N, 10.68. Found: C, 60.50; H, 6.97; N, 10.70.

EXAMPLE 24

Boc-Ile-Ile-OH.DCHA (XXV)

H-Ile-OH (1.97g, 15 mmol) fine powder was suspended in DMF (100 ml) and cooled to 0° C. Boc-Ile-OSu (4.92g, 15 mmol) and Et$_3$N (1.12 ml, 8 mmol) were added. The mixture was stirred for 2 hr at 0° C and 5 days at room temperature during which time the pH was kept near 8 by addition of Et$_3$N (0.98 ml, 7 mmol). The insoluble material was filtered off and the filtrate evaporated to dryness. The residue was treated with 0.5N HCl and the precipitate was extracted with EtOAc. The organic layer was washed with 0.5 N HCl H$_2$O, dried (Na$_2$SO$_4$) and concentrated to a smaller volume. Petroleum ether was added. The separated syrup failed to crystallize. It was redissolved in EtOAc and titrated with DCHA to pH 8. The precipitated crystalline salt was filtered and washed with EtOAc, yield 4.58g; mp 160°–162° C; $[\alpha]_D^{25}$ −18.5° (c 2, MeOH). Anal. Calcd for C$_{29}$H$_{55}$N$_3$O$_5$ (525.783): C, 66.25; H, 10.54; N, 7.99. Found: C, 66.03; H, 10.57; N, 7.94.

EXAMPLE 25

Boc-Ile-Ile-Lys(Z)-Asn-Ala-OBzl (XXVI)

Boc-Lys(Z)-Asn-Ala-OBzl (XXIV) (3.94g, 6 mmol) was treated with 0.4M BF$_3$·OEt$_2$ in glacial AcOH (60 ml) for 2.5 hr at room temperature. After evaporation to dryness, the residue was treated with dry ether, filtered, washed with dry ether, and the white powder dried over P$_2$O$_5$ and KOH. Boc-Ile-Ile-OH.DCHA (XXV) (3.16g, 6 mmol) was treated in EtOAc with 0.1N H$_2$SO$_4$, and the organic phase was washed with water, dried (Na$_2$SO$_4$), and evaporated. The resultant white solid was dissolved in DMF (45 ml) and cooled to 0° C. To this solution, were added successively with stirring: the above described salt, NMM dropwise to pH 7.0, HOBt (1.95g, 12 mmol) and DCC (1.36g, 6.6 mmol). pH was adjusted to 8.0 by addition of NMM (1.5 ml). The mixture was stirred for 2 hr at 0° C and for 2 days at room temperature. The precipitated by-products were filtered off and washed thoroughly with DMF. The combined filtrates were evaporated to a smaller volume. The product (XXVI) precipitated by treatment with 0.1N H$_2$SO$_4$ was filtered, washed with H$_2$O, 2% NaHCO$_3$ and H$_2$O. The obtained white solid (5g) mp 198°–203° C was repeatedly precipitated from DMF-isopropanol to yield 3.24g (61.2%); mp 222°–224° C; $[\alpha]_D^{25}$ −20.1° (c 1.5, DMF). Anal. Calcd for C$_{45}$H$_{67}$N$_7$O$_{11}$ (882.087): C, 61.27; H, 7.66; N, 11.12. Found: C, 61.59; H, 7.80; N, 11.09.

EXAMPLE 26

Boc-Ile-Ile-Lys(Z)-Asn-Ala-NHNH$_2$(XXVII)

Boc-Ile-Ile-Lys(Z)-Asn-Ala-OBzl (XXVI) (0.88g, 1 mmol) was dissolved in DMF (20 ml) and treated with H$_2$NNH$_2$ (0.50 ml) for 2 days at room temperature. To the cloudy mixture, MeOH was added and after standing for 2 hr in refrigerator the formed white solid was filtered and washed with MeOH and ether, yield 0.61g (75.7%); mp 252°–253° C; $[\alpha]_D^{25}$ −33.7° (c 1, DMSO). Anal. Calcd for C$_{38}$H$_{63}$N$_9$O$_{10}$ (805.993): C, 56.63; H, 7.88; N, 15.64. Found: C, 56.79; H, 7.91; N, 15.64.

EXAMPLE 27

Boc-Ile-Ile-Lys(Z)-Asn-Ala-Tyr(Bzl)-Lys(Z)-Lys(Z)-Gly-Glu(OBzl)-OBzl (XXVIII)

Box-Tyr(Bzl)-Lys(Z)-Lys(Z)-Gly-Glu(OBzl)-OBzl (XXII) (0.87g, 0.69 mmol) was treated for 4 hours with 0.4M BF$_3$.OEt$_2$ in AcOH (6.9 ml). The material obtained after evaporation and trituration with ether was directly used for coupling. Boc-Ile-Ile-Lys(Z)-Asn-Ala-NHNH$_2$ (XXVII) (0.556g, 0.69 mmol) was suspended in DMF (6.5 ml) and treated with 3.32N HCl (1.04 ml) and i-amylnitrite (0.14 ml) at −20° C for 30 min. After lowering the temperature of the bath to −30° C, Et$_3$N (0.483 ml, 3.45 mmol) was added followed by a precooled mixture of the salt of the pentapeptide, described above, in DMF (2.5 ml) pretreated with Et$_3$N (0.097 ml, 0.69 mmol). The temperature was maintained at −20° to −15° for 1 hr. The mixture was then stirred for 3 days at 0° C while the reaction mixture was kept at pH 8 by addition of Et$_3$N. After 5 hr the product started to precipitate in gelatinous form. It was acidified to pH 5 to 6 with a few drops of glacial AcOH. The solvent was evaporated to a smaller volume. The ensuing product was triturated with 0.05N HCl, filtered, and washed with H$_2$O to yield 1.25g. Alternatively, the product precipitated from the reaction mixture was collected by filtration and the mother liquor processed as described. Reprecipitation from DMSO-EtOH provided 0.92g (69%); mp 239°–241° C dec.; $[\alpha]_D^{25}$ −18.5° (c 0.99, DMSO). Anal. Calcd for C$_{103}$H$_{134}$N$_{14}$O$_{23}$ (1936.317): C, 63.89; H, 6.98; N, 10.13. Found: C, 63.72; H, 7.00; N, 9.98. Amino Acid Analysis (6N HCl-phenol, 100° C, 24 hr): Lys$_{3.15}$, Asp$_{1.00}$, Glu$_{1.03}$, Gly$_{1.00}$ Ala$_{0.97}$, Ile$_{1.93}$, Tyr$_{0.95}$.

EXAMPLE 28

Box-Lys(Z)-Asn-Ala-NHNH$_2$(XXIX)

Box-Lys(Z)-Asn-Ala-OBzl (XXIV) (2.3g, 3.5 mmol) was dissolved in MeOH (20 ml) with heating and treated with H$_2$NNH$_2$ (1.1 ml) at 4° C for 72 hr. The precipitated product was filtered and washed with MeOH and ether, yield 1.0g (49.3%). The white powder was crystallized from DMF with isopropanol; mp 177°–180° C; $[\alpha]_D^{25}$ −14.9° (c 1.5, DMF). Anal. Calcd for C$_{26}$H$_{41}$N$_7$O$_8$ (579.67): C, 53.87; H, 7.13; N, 16.91. Found: C, 53.75; H, 7.19; N, 17.00.

EXAMPLE 29

Boc-Lys(Z)-Asn-Ala-Ile-Ile-Lys(Z)-Asn-Ala-Tyr(Bzl)-Lys(Z)-Lys(Z)-Gly-Glu(OBzl)-OBzl (XXX)

(A) Cleavage of N$^\alpha$-Boc group from decapeptide (XXVIII).

Compound (XXVIII) (3.87g, 2 mmol) was treated with 98% HCOOH (35 ml) for 3.5 hr at room temperature. Excess HCOOH was then evaporated (at a bath temperature below 30° C). The residue was re-evaporated from DMF and treated with dry ether. The resulting white solid was dissolved with warming in DMF-DMSO (1:1, 50 ml). The decapeptide amine was precipitated by adjusting the pH to 8 with 0.5N NH$_4$OH, and isolated by repeated centrification and washing to yield after drying in a dessicator (KOH, H$_2$SO$_4$) a white powder, 3.22g (87.7%).

(B) Azide Coupling

Boc-Lys(Z)-Asn-Ala-NHNH$_2$ (XXIX) (2.32g, 4 mmol) was dissolved in DMF (15 ml) cooled to −20° C and treated with 3.8N HCl/THF (5.2 ml), followed by i-amylnitrite (0.8 ml, 6 mmol). After stirring at −20° C for 30 minutes the temperature was lowered to −30° C. Et$_3$N (2.8 ml, 20 mmol) was added followed by the pre-cooled solution of the decapeptide amine in DMF-DMSO (10:3, 13 ml). The pH was adjusted to 8 by addition of Et$_3$N. The mixture was stirred for 1 hr at −15° C and 4 days at 4° C. It was acidified with glacial AcOH and evaporated to a smaller volume. The product was precipitated with 1M AcOH, filtered, and washed thoroughly with H$_2$O. After drying it was triturated with EtOH and with boiling MeOH to yield a white powder, 4.05g (97%, based on the decapeptide amine); mp 257°–259° C dec. Precipitation with 90% aq. MeOH from DMF-DMSO (1:1, 11ml) provided 3.45g of (XXX) with the same mp; $[\alpha]_D^{25}$ −24.8° (c 1, DMSO). Anal. Calcd for C$_{124}$H$_{163}$N$_{19}$O$_{29}$ (2383.82): C, 62.48; H, 6.89; N, 11.16. Found: C, 62.21; H, 6.76; N, 11.25. Amino Acid Analysis (6N HCl-phenol, 110° C, 25 hr): Lys$_{4.07}$, Asp$_{2.04}$, Glu$_{1.00}$, Gly$_{1.00}$, Ala$_{2.07}$, Ile$_{1.91}$, Tyr$_{0.91}$.

EXAMPLE 30

Boc-Ser(Bzl)-Gln-Thr(Bzl)-Pro-Leu-Val-Thr(Bzl)-Leu-Phe-Lys(Z)-Asn-Ala-Ile-Ile-Lys(Z)-Asn-Ala-Tyr(Bzl)-Lys(Z)-Lys(Z)-Gly-Glu(OBzl)-OBzl (XXXI)

(A) Cleavage of N$^\alpha$-Boc-group of the compound (XXX).

Compound (XXX) (0.429g, 0.18 mmol) was treated with 98% HCOOH (3 ml) as described for the compound (XXVIII) in Example 29 to yield a white solid, 3.9g (93%); mp 272°–275° C dec. The salt was titrated with 0.5N NH$_4$OH in DMF-DMSO (4:3, 7 ml) as described for (XXVIII) in Example 29 to yield a white powder; mp 261°–263° C dec.

(B) Fragment condensation (DCC-HOBt)

To a cold solution of Boc-Ser(Bzl)-Gln-Thr(Bzl)-Pro-Leu-Val-Thr(Bzl)-Leu-Phe-OH (XVII) (0.296g, 0.215 mmol) in DMF (3.5 ml), HOBt (0.07g, 0.43 mmol) was added, followed by DCC (0.049g, 0.236 mmol). The mixture was stirred for 1 hour at 0° C while pH 7 was maintained by addition of NMM. A pre-cooled solution of the tridecapeptide amine was added and the pH adjusted to 7–8 with NMM. Stirring was continued for 2 hours at 0° C and for 3 days at room temperature. The mixture was evaporated to a small volume and treated with 4% aq. NaHCO$_3$. The crude precipitate was filtered and washed with H$_2$O to neutral. After drying it was triturated repeatedly with boiling MeOH to produce a white powder, 0.452g (74% based on the tridecapeptide amine). Amino acid analysis (6N HCl-phenol, 110° C, 24 hr), Lys$_{3.8}$, Asp$_{2.03}$, Thr$_{1.64}$, Ser$_{0.83}$, Glu$_{2.12}$, Pro$_{1.00}$, Gly$_{1.08}$, Ala$_{2.07}$, Val$_{1.06}$, Ile$_{2.00}$, Leu$_{1.96}$, Tyr$_{0.99}$, Phe$_{1.00}$. For elemental analysis a sample was freeze-dried from DMSO; mp sintered 283°–290° dec. $[\alpha]_D^{25}$ −23.8° (c 0.5, DMSO). Anal. Calcd for C$_{192}$H$_{255}$N$_{29}$O$_{42}$ (3641.384): C, 63.33; H, 7.06; N, 11.16. Found: C, 61.16; H, 7.07; N, 10.96.

EXAMPLE 31

Z-Tyr-Gly-Gly-Phe-Met-Thr(Bzl)-Ser(Bzl)-Glu(OBzl)-Lys(Z)-Ser(Bzl)-Gln-Thr(Bzl)-Pro-Leu-Val-Thr(Bzl)-Leu-Phe-Lys(Z)-Asn-Ala-Ile-Ile-Lys(Z)-Asn-Ala-Tyr(Bzl)-Lys(Z)-Lys(Z)-Gly-Glu(OBzl)-OBzl (XXXII)

(A) Cleavage of N$^\alpha$-Boc-group of (XXXI)

Compound (XXXI) (0.2913g, 0.08 mmol) was treated with 98% HCOOH (2 ml) for 3.5 hr at room temperature. After filtration and concentration to a small volume, the residue was dissolved in DMSO-DMF (3:1, 4 ml) and a few drops of Et$_3$N was added. It was then titrated with 0.5N NH$_4$OH to pH 8. The precipitated 22 residue peptide amine was filtered, washed thoroughly with H$_2$O to neutral, and dried over KOH and H$_2$SO$_4$.

(B) Fragment condensation (DCC-HOBt)

Z-Tyr-Gly-Gly-Phe-Met-Thr(Bzl)-Ser(Bzl)-Glu(OBzl)-Lys(Z)-OH (VI) (0.311g, 0.2 mmol) was dissolved in DMF (2 ml) and the solution was cooled to 0° C. HOBt (0.065g, 0.4 mmol) was added, followed by DCC (0.045g, 0.22 mmol). The mixture was stirred for 1 hour at 0° C and for 1 hour at room temperature. It was then added to a solution of the above docosapeptide amine dissolved in molten phenol. The mixture was stirred for 3 days at room temperature. It was poured slowly to a stirred, cold (0° C), solution of 0.5% AcOH (200 ml). The precipitated solid was filtered and washed with H$_2$O and EtOH. The crude product was triturated three times with boiling MeOH, centrifuged, and dried. Precipitation from DMF/MeOH provided 0.20g (50%); mp 275°–279° C dec. The material was without further characterization subjected to complete protecting group removal with liquid HF.

EXAMPLE 32

$\beta_h$-Endorphin

Protected $\beta_h$ endorphin (XXXII) (70 mg, 0.0138 mmol) was treated in HF (2.5 ml) for 45 minutes at 0° C in the presence of anisole (0.5 ml) and diethylsulfide (1 ml). After evaporation of HF, the residue was taken up in 1 M AcOH (5 ml) and the aqueous phase was extracted 3 times with peroxide free ether. The ether extracts were backextracted with 1M AcOH. The combined aqueous extracts were lyophilized to provide a white powder 53 mg. A portion (23 mg) was subjected to gel filtration on a 1 × 94 cm column of Sephadex G-15 in 0.5N AcOH. One unsymmetrical peak was obtained. Lyophilization of the pooled fractions from the faster eluting half of the peak yielded 8.9 mg. A portion of this material (3.9 mg) was further purified by partition chromatography on a 0.6 × 50 cm column of Sephadex G-50 super fine, in a solvent system n BuOH-pyridine-0.6 M NH$_4$Ac (5:3:10) to give a major peak which eluted at a position identical to that of genuine $\beta_h$-endorphin (Rf 0.4). Lyophilization provided 1.9 mg of purified $\beta_h$-endorphin.

Alternatively, a portion of the material obtained from the gel filtration was chromatographed on a 0.6 × 100 cm column of Dextran CPG-550 equilibrated with a 9:1 mixture of acetonitrile - 0.1M NH$_4$OAc, pH 7 and eluted with a convex gradient generated from 200 ml of 9:1 mixture and 200 ml of O.1M NH$_4$OAc pH 7. One single peak was eluted with identical elution characteristics as a standard human $\beta$-endorphin.

We claim:
1. A compound of the formula

R¹-Try(R²)-Gly-Gly-Phe-Met-Thr(R³)-Ser(R⁸)-Glu(OR⁴)-Lys(R⁵)-Ser(R⁸)-Gln(R⁶)-Thr(R³)-Pro-Leu-Val-Thr(R³)-Leu-Phe-Lys(R⁵)-Asn(R⁶)-Ala-Ile-Ile-Lys(R⁵)-Asn(R⁶)-Ala-Tyr(R²)-Lys(R⁵)-Lys(R⁵)-Gly-Glu((OR⁴)-OR⁷ where R¹ is a conventional α-amino protecting group, R² is hydrogen or a conventional protecting group for the phenolic hydroxyl group of the tyrosine residue, R³ is hydrogen or a conventional protecting group for the hydroxyl group of the threonine residue, R⁴ is hydrogen or a conventional carboxyl protecting group, R⁵ is a conventional ω-amino protecting group, R⁶ is hydrogen or a conventional protecting group for the carboxamide group, R⁷ is hydrogen or a conventional carboxyl protecting group and R⁸ is hydrogen or a conventional protecting group for the hydroxyl group of the serine residue.

2. The compound of claim 1 wherein R¹ is benzyloxycarbonyl, R² is hydrogen, R³ is benzyl, R⁴ is benzyl, R⁵ is benzyloxycarbonyl, R⁶ is hydrogen, R⁷ is benzyl and R⁸ is benzyl.

3. A compound of the formula

R¹-Tyr(R²)-Gly-Gly-Phe-Met-Thr(R³)-Ser(R⁸)-Glu(OR⁴)-Lys(R⁵)-OH where R¹ is a conventional α-amino protecting group, R² is hydrogen or a conventional protecting group for the phenolic hydroxyl group of the tyrosine residue, R³ is hydrogen or a conventional protecting group for the hydroxyl group of the threonine residue, R⁴ is hydrogen or a conventional carboxyl protecting group and R⁸ is hydrogen or a conventional protecting group for the hydroxyl group of the serine residue.

4. The compound of claim 3 wherein R¹ is benzyloxycarbonyl, R² is hydrogen, R³ is benzyl, R⁴ is benzyl, R⁵ is benzyloxycarbonyl and R⁸ is benzyl.

5. A compound of the formula

A-Ser(R⁸)-Gln(R⁶)-Thr(R³)-Pro-Leu-Val-Thr(R³)-Leu-Phe-Lys(R⁵)-Asn(R⁶)-Ala-Ile-Ile-Lys(R⁵)-Asn(R⁶)-Ala-Tyr(R²)-Lys(R⁵)-Lys(R⁵)-Gly-Glu(OR⁴)-OR⁷ where A is hydrogen or a conventional α-amino protecting group, R² is hydrogen or a conventional protecting group for the phenolic hydroxyl group of the tyrosine residue, R³ is hydrogen or a conventional protecting group for the hydroxyl group of the threonine residue, R⁴ is hydrogen or a conventional carboxyl protecting group, R⁵ is a conventional ω-amino protecting group, R⁶ is hydrogen or a conventional protecting group for the carboxamide group, R⁷ is hydrogen or a conventional carboxyl protecting group and R⁸ is hydrogen or a conventional protecting group for the hydroxyl group of the serine residue.

6. The compound of claim 5 wherein A is hydrogen, R² is hydrogen, R³ is benzyl, R⁴ is benzyl, R⁵ is benzyloxycarbonyl, R⁶ is hydrogen, R⁷ is benzyl and R⁸ is benzyl.

7. The compound of claim 5 wherein A is benzyloxycarbonyl, R² is hydrogen, R³ is benzyl, R⁴ is benzyl, R⁵ is benzyloxycarbonyl, R⁶ is hydrogen, R⁷ is benzyl and R⁸ is benzyl.

8. A compound of the formula

B-Lys(R⁵)-Asn(R⁶)-Ala-Ile-Ile-Lys(R⁵)-Asn(R⁶)-Ala-Tyr(R²)-Lys(R⁵)-Lys(R⁵)-Gly-Glu(OR⁴)-OR⁷ where B is hydrogen or a conventional α-amino protecting group, R² is hydrogen or a conventional protecting group for the phenolic hydroxyl group of the tyrosine residue, R⁴ is hydrogen or a conventional carboxyl protecting group, R⁵ is a conventional ω-amino protecting group, R⁶ is hydrogen or a conventional protecting group for the carboxamide group and R⁷ is hydrogen or a conventional carboxyl protecting group.

9. The compound of claim 8 wherein B is hydrogen, R² is hydrogen, R⁴ is benzyl, R⁵ is benzyloxycarbonyl, R⁶ is hydrogen and R⁷ is benzyl.

10. The compound of claim 8 wherein B is benzyloxycarbonyl, R² is hydrogen, R⁴ is benzyl, R⁵ is benzyloxycarbonyl, R⁶ is hydrogen and R⁷ is benzyl.

11. A compound of the formula

A-Ser(R⁸)-Gln(R⁶)-Thr(R³)-Pro-Leu-Val-Thr(R³)-Leu-Phe-OH where A is hydrogen or a conventional α-amino protecting group, R³ is hydrogen or a conventional protecting group for the hydroxyl group of the threonine residue, R⁶ is hydrogen or a conventional protecting group for the carboxamide group and R⁸ is hydrogen or a conventional protecting group for the hydroxyl group of the serine residue.

12. The compound of claim 11 wherein A is hydrogen, R³ is benzyl, R⁶ is hydrogen and R⁸ is benzyl.

13. The compound of claim 11 wherein A is benzyloxycarbonyl, R³ is benzyl, R⁶ is hydrogen and R⁸ is benzyl.

14. A process for the preparation of human β-endorphin which process comprises in combination:
(A) reacting a protected nonapeptide of the formula R¹-Try(R²)-Gly-Gly-Phe-Met-Thr(R³)-Ser(R⁸)-Glu(OR⁴)-Lys(R⁵)-OH, where R¹ is a conventional α-amino protecting group, R² is hydrogen or a conventional protecting group for the phenolic hydroxyl group of the tyrosine residue, R³ is hydrogen or a conventional protecting group for the hydroxyl group of the threonine residue, R⁴ is hydrogen or a conventional carboxyl protecting group, R⁵ is a conventional ω-amino protecting group and R⁸ is hydrogen or a conventional protecting group for the hydroxyl group of the serine residue with a 22 amino acid partially protected peptide amine of the formula H₂N-Ser(R⁸)-Gln(R⁶)-Thr(R³)-Pro-Leu-Val-Thr(R³)-Leu-Phe-Lys(R⁵)-Asn(R⁶)-Ala-Ile-Ile-Lys(R⁵)-Asn(R⁶)-Ala-Tyr(R²)-Lys(R⁵)-Lys(R⁵)-Gly-Glu(OR⁴)-OR⁷ where R¹, R², R³, R⁴, R⁵ and R⁸ are as above and R⁶ is hydrogen or a conventional protecting group for the carboxamide group and R⁷ is hydrogen or a conventional carboxyl protecting group
under peptide bond forming conditions consisting of treatment with dicyclohexylcarbodiimide/1-hydroxybenzotriazole so as to produce a compound of the formula R¹-Tyr(R²)-Gly-Gly-Phe-Met-Thr(R³)-Ser(R⁸)-Glu(OR⁴)-Lys(R⁵)-Ser(R⁸)-Gln(R⁶)-Thr(R³)-Pro-Leu-Val-Thr(R³)-Leu-Phe-Lys(R⁵)-Asn(R⁶)-Ala-Ile-Ile-Lys(R⁵)-Asn(R⁶)-Ala-Tyr(R²)-Lys(R⁵)-Lys(R⁵)-Gly-Glu(OR⁴)-OR⁷ where R¹, R², R³, R⁴, R⁵, R⁶, R⁷ and R⁸ are as above; and
(B) removing the protective groups with strong acid so as to yield the desired human β-endorphin.

* * * * *